Figure 1:
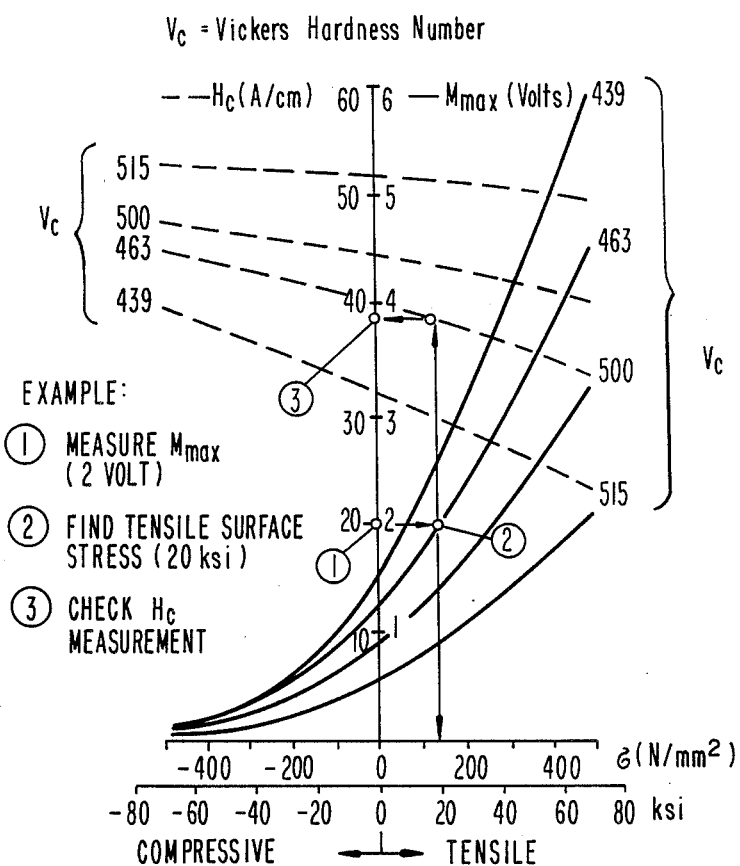

United States Patent [19]

Stuecker et al.

[11] Patent Number: 4,881,030

[45] Date of Patent: Nov. 14, 1989

[54] METHOD AND APPARATUS FOR MEASURING AND PRECISELY LOCATING INTERNAL TENSILE STRESSES IN HARDENED REGIONS OF COMPONENTS BY MEASURING COERCIVE FIELD STRENGTH AND BARKHAUSEN NOISE AMPLITUDE

[75] Inventors: Erwin Stuecker, Essen-Frintrop; Gerhard Hofer, Roettenbach; Dietmar Koch, Muelheim an der Ruhr; Uenal Guenes, Erlangen, all of Fed. Rep. of Germany

[73] Assignee: Siemens Aktinegesellschaft, Munich, Fed. Rep. of Germany

[21] Appl. No.: 182,845

[22] Filed: Apr. 18, 1988

[30] Foreign Application Priority Data

Apr. 16, 1987 [DE] Fed. Rep. of Germany ....... 3713062

[51] Int. Cl.⁴ .................... G01B 7/24; G01N 27/72; G01R 33/00; G01R 35/00
[52] U.S. Cl. ................................ 324/209; 324/202; 324/227
[58] Field of Search ............... 324/202, 209, 227; 73/801, 802, 660; 364/508, 551.01, 551.02, 571.07

[56] References Cited

U.S. PATENT DOCUMENTS

| | | |
|---|---|---|
| 3,697,866 | 10/1972 | Kanda et al. |
| 4,692,701 | 9/1987 | Dundas et al. ................. 324/209 |
| 4,771,237 | 9/1988 | Daley .......................... 324/202 |

FOREIGN PATENT DOCUMENTS

| | | |
|---|---|---|
| 0100009 | 2/1984 | European Pat. Off. . |
| 2247634 | 5/1973 | Fed. Rep. of Germany . |
| 2837733 | 3/1980 | Fed. Rep. of Germany . |
| 3037932 | 7/1985 | Fed. Rep. of Germany . |
| 2158994 | 6/1973 | France . |

*Primary Examiner*—Reinhard J. Eisenzopf
*Assistant Examiner*—Walter E. Snow
*Attorney, Agent, or Firm*—Herbert L. Lerner; Laurence A. Greenberg

[57] ABSTRACT

A method and apparatus for ascertaining internal stresses in a hardened region to be tested for a component made of a predetermined material includes measuring coercive field strength and amplitude of magnetic Barkhausen noise as a function of mechanical stress and hardness in calibration samples of a predetermined material of known hardness and known internal stress. Calibration functions are ascertained from the measured values indicating the dependency of the hardness and the amplitude of the magnetic Barkhausen noise as functions of the hardness and mechanical stress. The coercive field strength and the amplitude of the magnetic Barkhausen noise is measured in a location-dependent manner over the region of the component to be tested. The measured values of the coercive field strength and the amplitude of the magnetic Barkhausen noise are converted in the region to be tested into location-dependent hardness and into location-dependent mechanical stress using the ascertained calibration functions. The location-dependent mechanical stress and the location-dependent hardness in the region to be tested are present independently of one another and are available for further processing.

16 Claims, 2 Drawing Sheets

METHOD AND APPARATUS FOR MEASURING AND PRECISELY LOCATING INTERNAL TENSILE STRESSES IN HARDENED REGIONS OF COMPONENTS BY MEASURING COERCIVE FIELD STRENGTH AND BARKHAUSEN NOISE AMPLITUDE

The invention relates to a method for measuring internal stresses in a hardened region to be tested of a component made of a predetermined material, in particular a turbine blade, and an apparatus for performing the method having an exciter and a measurement pickup system for measuring the amplitude of the magnetic Barkhausen noise and/or the coercive field strength.

German Published, Non-Prosecuted Application DE-A No. 28 37 733, German Patent DE-C No. 2 30 37 932 and European Patent Application EP-A No. 1 0 100 009 disclose measuring methods for ascertaining the status of materials that utilize the Barkhausen effect, or which permit a determination of the coercive field strength. German Published, Non-Prosecuted Application DE-A No. 22 47 634 also discloses the application of the measurements for the purpose of quality control of soft unalloyed steels.

A measuring instrument of this kind has been developed by the Fraunhofer Gesellschaft zur Förderung der angewandten Forschung e. V. (Fraunhofer Institute For Applied Research). This instrument, called an "EMAG analyzer" is, for instance, suitable for making the necessary measurements for the present invention. The measuring principle is described in detail in the directions for operating the "EMAG analyzer E2302 S8200" instrument. The principles of the necessary measurements are also described in the specifications of the two patent applications mentioned above, which are expressly incorporated by reference herein.

The paper "Quality Control of Last Stage Blades with Flame Hardened Leading Edges" presented at the joint ASME/IEEE Power Generation Conference, Miami Beach, Fla., Oct. 4–8, 1987, describes in detail the problems encountered with flame hardened blades relating to stress corrosion cracking as well as X-ray and electro-magnetic measuring devices for inspecting such blades. The principle of X-ray Goniometry measurement and evaluation, the application of X-ray techniques as well as electromagnetic effects described herein, are described in detail in the paper.

In the prior art, qualitative information on mechanical stresses in a component can be obtained by measuring the magnetic Barkhausen noise amplitude, and qualitative determinations of the hardness can be obtained by measuring the coercive field strength. In workpieces having especially hardened regions, such as turbine blades having hardened leading edges, such qualitative findings are generally inadequate for determining engineering safety. This is because both the hardness and the mechanical stress of the region to be tested affect the two measured values mentioned above. On the other hand, since the hardness of a region to be tested is generally neither known precisely, nor constant over the entire region, conventional methods are unable to provide quantitative information on existing mechanical stresses and the distribution thereof in a component.

However, since on the other hand the presence of internal compressive stresses in heavy-duty components such as turbine blades can promote the later formation of cracks, it is necessary to provide very precise quantitative measurements for quality control of components after manufacture or in iterative tests.

It is accordingly an object of the invention to provide a measuring method and apparatus for measuring and precisely locating internal tensile stresses in hardened regions of components, which overcomes the hereinafore-mentioned disadvantages of the heretofore-known methods and devices of this general type, which permits a quantitative measurement of internal stresses and which therefore especially allows precise location of internal tensile stresses. Sites having high internal tensile stresses or cracks that have already started to form, should be reliably recognized.

With the foregoing and other objects in view there is provided, in accordance with the invention, a method for ascertaining internal stresses in a hardened region to be tested of a component, especially a turbine blade, made of a predetermined material, which comprises measuring coercive field strength and amplitude of magnetic Barkhausen noise as a function of mechanical stress and hardness in calibration samples of a predetermined material of known hardness and known internal stress such as X20Cr13 or X10CrNiMo V12 22; ascertaining calibration functions from the measured values indicating the dependency of the hardness and the amplitude of the magnetic Barkhausen noise as functions of the hardness and mechanical stress; measuring the coercive field strength and the amplitude of the magnetic Barkhausen noise in a location-dependent manner over the region of the component to be tested; converting the measured values of the coercive field strength and the amplitude of the magnetic Barkhausen noise in the region to be tested into location-dependent hardness, such as Vickers hardness, and into location-dependent mechanical stress using the ascertained calibration functions, and providing the location-dependent mechanical stress and the location-dependent hardness in the region to be tested independently of one another and in a form available for further processing, especially for a visual display of the stress distribution or for further processing in a computer.

The invention is based on the recognition that the dependency of the coercive field strength and of the Barkhausen noise on the mechanical stress and the hardness can be ascertained in principle by suitable calibration samples for each material. A relationship between these variables that can be represented as a family of curves, as diagrams, or in the form of a function is then obtained. It has now been demonstrated that when this relationship is learned from measuring the coercive field strength and the magnetic Barkhausen noise amplitude, both the local hardness and the mechanical stress prevailing there are ascertainable. This makes it possible to obtain exact quantitative information, especially regarding the existing internal stresses in a component, regardless of the locally present hardness.

In accordance with another mode of the invention, there is provided a method which comprises selecting the region to be tested as the hardened leading edge of a turbine blade, especially a low-pressure turbine blade.

These heavy-duty components are tested regularly, and blades that threaten to become dangerous can be recognized sufficiently early with the measuring method according to the invention. In the prior art, endangered regions could possibly have been recognized by using a maximum of the Barkhausen noise amplitude, but it would hardly have been possible to ascertain the absolute magnitude of the internal tensile stresses, because of the influence of the variable hardness, which previously could not be eliminated. On the contrary, in the measurement of the actual mechanical stresses according to the invention, absolute values can be determined. As a result, endangered regions which would only have exhibited an unremarkable Barkhausen noise amplitude in the prior art, due to the contrary behavior of hardness and internal compressive stress, can now be discovered.

Tests have also shown that in regions in which internal tensile stresses have already led to small cracks, typical double maximums of the measured mechanical stresses result if a measuring system is moved over such a region.

In accordance with a further mode of the invention, there is provided a method which comprises moving an exciter and a measurement pickup system at a defined and preferably constant speed on a defined measurement path or track in the region to be tested with measurements being performed in rapid succession, and obtaining a local association of the measured values from the chronological succession thereof as a result of the movement, since the speed is known. This is done in order to enable systematic testing of the local distribution of mechanical stresses. This kind of method is particularly suitable for testing the hardened edge of a turbine blade.

With the objects of the invention in view, there is also provided an apparatus for ascertaining internal stresses in a hardened region to be tested of a component made of a predetermined material, comprising: an exciter system and a measurement pickup system measuring at least one of amplitude of magnetic Barkhausen noise and/or coercive field strength and producing measured values; electronic evaluation means connected to the measurement pickup system for processing the measured values of the coercive field strength and the amplitude of the magnetic Barkhausen noise in parallel; the electronic evaluation means including at least one memory having calibration data or calibration functions for at least one material relating to dependencies between the Barkhausen noise amplitude the coercive field strength, the hardness and the mechanical stress; and the electronic evaluation means including a conversion stage converting the measured values into material properties of hardness and stress using the calibration data stored the at least one memory.

In accordance with another feature of the invention, the exciter system and the measurement pickup system are movable along a defined measurement track at a defined speed in a region of a component, especially a turbine blade, to be tested.

In accordance with a further feature of the invention, the exciter system is a magnetic exciter system also forming a magnetic holder for the measurement pickup system on the component to be tested.

In accordance with a concomitant feature of the invention, the magnetic exciter system includes a magnet yoke having two magnetic poles between which the measurement pickup system is movable.

As shown in further detail in the drawing, an apparatus according to the invention must include a memory having calibration data and a conversion stage, in order to ascertain the two independent material properties, which are hardness and mechanical stress, from the two non-independent measured values of coercive field strength and Barkhausen noise amplitude. The measured values should preferably be processed on line, in order to shorten component testing times. In order to test larger regions, such as the edges of low-pressure turbine blades, an exciter and measurement pickup system must be moved along the region to be tested, preferably at a constant speed; this can be attained by means of a mechanical drive mechanism or a suitable manipulator. In the case of the leading edge of a turbine blade, such a manipulator can, for instance, "ride" the edge to be tested. In other components to be tested, it is also possible for the exciter system, which substantially includes a magnet yoke having a magnetic coil, to be firmly attached to the component by the magnetic action thereof. In such a case the measurement pickup system can then be supported by the exciter system and moved between the two poles.

Other features which are considered as characteristic for the invention are set forth in the appended claims.

Although the invention is illustrated and described herein as embodied in a measuring method and apparatus for measuring and precisely locating internal tensile stresses in hardened regions of components, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

Figure 2:
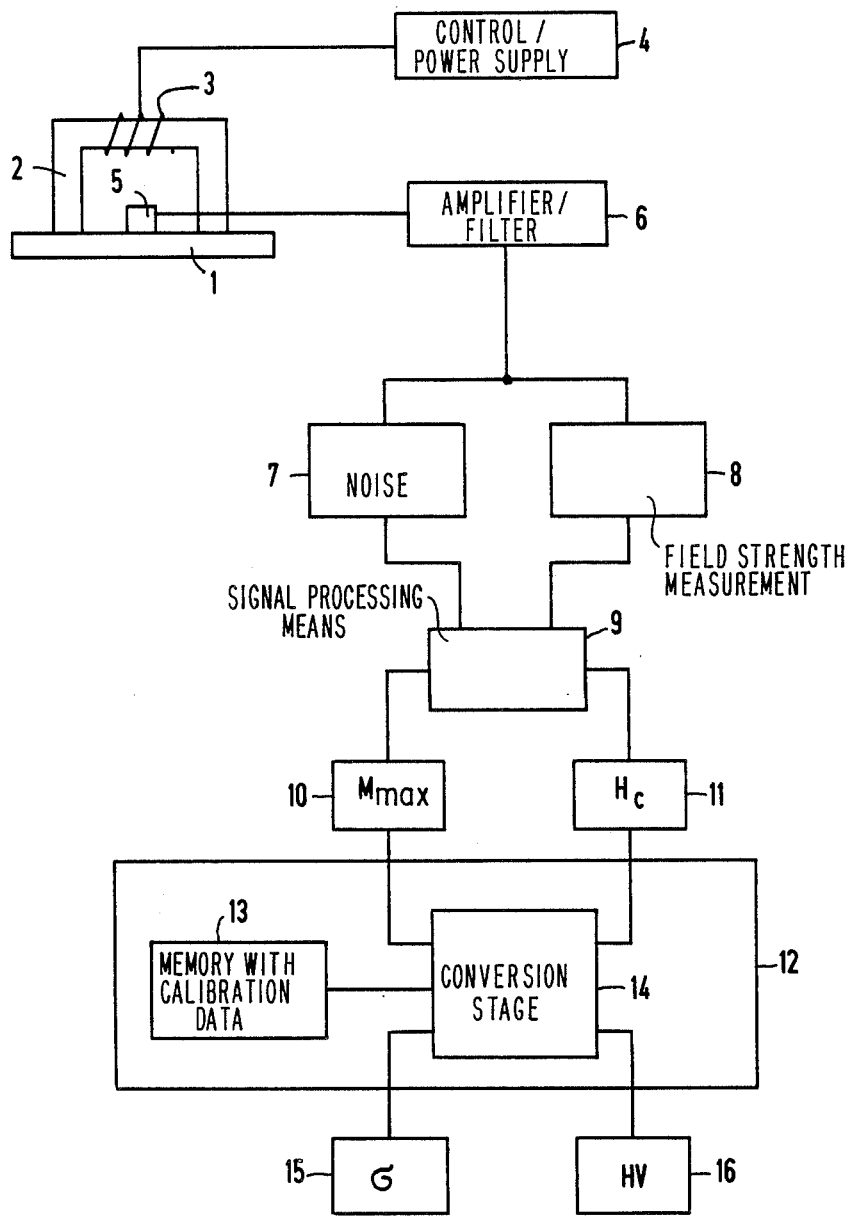

FIG. 1 is a graph showing surface stress as a function of Vickers Hardness for X20Cr13; and FIG. 2 is a diagrammatic view and a block circuit diagram of the apparatus according to the invention.

Referring now to the figures of the drawings in detail and first, particularly, to FIG. 1 thereof, a background of the principles used according to the invention will first be given. In the 1970s, the first investigations were published which discussed the stress-related results of the Barkhausen noise effect on ferritic gas turbine blades. The Fraunhofer Institute of Nondestructive Testing in Saarbruecken, West Germany developed an "EMAG-Analyzer" that measures both the Barkhausen noise amplitude and the coercive field strength simultaneously.

Since the Barkhausen noise amplitude is sensitive to applied stresses and the coercive field strength is sensitive to the material composition, it was possible to develop a calibration method in order to obtain quantitative results. After the development of the transmitter and pick-up system, this method was used on calibration fixtures and on actual turbine blades. A U-shaped electro-magnet produces an alternating field (180°) at excitation frequencies from 20 to 100 Hz. The Barkhausen noise amplitude is detected with an air coil and coercive field strength with a Hall probe. These are both located between the magnetic poles. Their position can be varied in both X and Y axes. After the reversal of the alternating field, the local Barkhausen noise signal and the tangential H-field strength are measured digitally and printed as $M_{max}$ in volts and $H_c$ in A/cm. The following investigations were performed with an excitation frequency of 30 Hz. Digital outputs are obtained from the average value of every 10 cycles.

Calibration of $M_{max}$ and $H_c$

The calibration on material samples of X20Cr13 was performed with bending probes that were flame hardened in a water bath, in exactly the same manner as the turbine blades. After that different treatments are used to achieve different surface hardnesses. Tensile and compressive stresses of up to $\pm 500$ N/mm$^2$ ($\pm 73$ ksi) can be produced with this calibration equipment. The stresses induced are measured with strain gauges and the Vickers hardness of the samples is determined with a Wolpert hardness tester.

When the magnetic field is reversed by 180° the intensity of the Barkhausen noise increases with the presence of tensile stresses. Consequently, the intensity of $M_{max}$ diminishes with compressive stresses. This allows the coercive field amplitude, $H_c$, to be read directly from the location of the maximum of the Barkhausen noise amplitude, $M_{max}$. This gives the strength of the magnetic counter field that is produced by the alternating magnetic field.

FIG. 1 depicts the relationship between Vickers hardness and applied stress for the blade material X20Cr13. One can clearly see from this figure that the amplitude of $M_{max}$ increases with increasing tensile stresses. With decreasing hardness the signals become larger. The coercive field strength increases with increasing surface hardness. There is, however, a larger effect with increasing tensile stresses. Only relevant hardness values were investigated. These are values normally obtained in the manufacturing process of turbine blades. In order to minimize measurement uncertainty in residual stress measurements on hardened blade materials, it is absolutely necessary to carry out such calibration measurements. Through the use of such calibration curves it is possible, either manually or with a computer, to perform investigations in the factory and inspections in power plants during turbine outages.

Testing of Turbine Blades

Test equipment has been developed by the firm Kraftwerk Union A.G. of Muelheim/Ruhr, West Germany. It consists of two flight cases, and weighs approximately 160 kg (320 lbs). One case contains the "EMAG" Analyzer, the pick-up and an oscilloscope. The second case holds a Hewlett-Packard 3000/900 computer and data acquisition system with a dual diskette drive for data storage, a color monitor, a printer and an X-Y plotter. The entire device is portable and can operate on either 220 volt, 50 hz, or a 110 volt, 60 Hz electrical power supply. This mobile device in-service inspections of turbine blades with hardened leading edges to be performed in power plants.

Two technicians are required for an inspection. One is needed to position the pick-up on the last stage blade leading edge, while the other individual operates the data acquisition equipment. The pick-up moves at a constant rate of from 1–5.3 mm/sec (0.04–0.21 in/sec) along the inlet edge of the blade. The distance from the blade leading edge can also be varied. A data cable length of 10 m (32.8 ft) allows complete access to either flow of even large LP turbines. The measurement is initiated by the pick-up operator, and the measured values of $M_{max}$ and $H_c$ are fed into the data acquisition system while being simultaneously displayed on the color monitor. After the measurement is completed, the maximum value of $M_{max}$, its corresponding value for the coercive field strength $H_c$, and its location from the blade tip are shown on the screen. This information can be documented on the X-Y plotter, if desired. This also includes a description which lists the unit name, blade material, blade number, blade location, etc. Since a single 3½ inch diskette can hold enough data for 100 measurements, it is possible, in most cases, to record the information for an entire blade row on a single diskette. This data can then be listed, in a simplified format, on the printer. This print-out provides a good overview of the entire blade row. It lists the blade number, data record number, the maximum values of $M_{max}$ and $H_c$ and the location from the blade tip.

There are two methods that can be used to calculate the residual stresses (G in N/mm$^2$ or ksi) and the Vickers hardness, (HV$_{10}$) from the measured values of $M_{max}$ and $H_c$. A simple manual evaluation can be performed, based on the calibration curves for $H_c$ and $M_{max}$. One normally just concentrates on the maximum $M_{max}$ value and determines the amount and type (tensile/compressive) of residual stress from the curves. This information and the location from the blade tip are then taken into consideration for the calculation of the blade vane total stress in the flame hardened region. The other method employs the computer and utilizes a matrix made form the calibration data. The stresses and Vickers hardness are then determined iteratively between the two neighboring calibration curves. The results can then be displayed on the monitor or printed on the X-Y plotter.

In the illustration of FIG. 2, the measuring principle is considered prior art up to the presence of the measured values for the coercive field strength and the maximum Barkhausen noise amplitude. In FIG. 2 there is seen a component 1 to be tested which is magnetized by means of an exciter system 2, 3, 4 having a magnetic alternating field. The exciter system includes a magnet yoke 2, a magnetic coil 3 and the associated current supply or control 4. A measurement pickup system 5 contains the conventional devices for measuring the Barkhausen noise and the coercive field strength, such as a magnetically inductive pickup and a Hall sensor. After passing through an amplification or filtration device 6, the measurement signals are supplied through separate lines 7, 8 for the Barkhausen noise and the coercive field strength to signal processing means 9, which are followed by signal outputs 10, 11 for the Barkhausen noise amplitude $M_{max}$ and the coercive field strength $H_c$. The two measured values are each separately dependent on both the hardness and the mechanical stresses of the components being tested. In order to obtain unambiguous information on the material properties, further electronic evaluation means 12 which include a memory having calibration data 13 and a conversion stage 14, therefore follow. By comparison with the material-specific calibration data or by conversion with corresponding calibration functions, which sufficiently precisely approximate the ascertained calibration data, the electronic evaluation means 12 can ascertain the two mutually independent material properties of hardness (HV) and mechanical stress (sigma) and they can be stored in memory, displayed or otherwise made visible in a suitable form at display devices 15, 16, respectively. In general, it is particularly informative and graphic to display these material values on a monitor as a function of the travel distance of the measurement pickup.

With the measuring method according to the invention, it is particularly possible to perform accurate measurements of internal tensile stresses in hardened regions which have a hardness that is not entirely constant. For example, turbine blades that have unfavorable material properties can be reliably recognized in this way and taken out of operation.

We claim:

1. Method for ascertaining internal stresses in a hardened region to be tested of a component made of a predetermined material, which comprises:
   (a) measuring coercive field strength and amplitude of magnetic Barkhausen noise as a function of mechanical stress and hardness in calibration samples of a predetermined material of known hardness and known internal stress;
   (b) ascertaining calibration functions from the measured values indicating the dependency of the hardness and the amplitude of the magnetic Barkhausen noise as functions of the hardness and mechanical stress;
   (c) measuring the coercive field strength and the amplitude of the magnetic Barkhausen noise in a location-dependent manner over the region of the component to be tested;
   (d) converting the measured values of the coercive field strength and the amplitude of the magnetic Barkhausen noise in the region to be tested into location-dependent hardness and into location-dependent mechanical stress using the ascertained calibration functions, and providing the location-dependent mechanical stress and the location-dependent hardness in the region to be tested independently of one another and in a form available for further processing.

2. Method according to claim 1, which comprises selecting a turbine blade as the component.

3. Method according to claim 1, which comprises selecting the predetermined material for the calibration samples from the group consisting of X20Cr13 and X10CrNiMo V12 22.

4. Method according to claim 1, which comprises converting the measured values of the coercive field strength and the amplitude of the magnetic Barkhausen noise into Vickers hardness.

5. Method according to claim 1, which comprises carrying out the further processing in the form of a visual display of the stress distribution.

6. Method according to claim 1, which comprises carrying out the further processing in a computer.

7. Method according to claim 1, which comprises selecting the region to be tested as the hardened leading edge of a turbine blade.

8. Method according to claim 1, which comprises selecting the region to be tested as the hardened leading edge of a low-pressure turbine blade.

9. Method according to claim claim 1, which comprises moving an exciter and a measurement pickup system at a defined speed on a defined measurement track in the region to be tested, and obtaining a local association of the measured values from the chronological succession thereof as a result of the movement.

10. Apparatus for ascertaining internal stresses in a hardened region to be tested of a component made of a predetermined material, comprising:
    (a) an exciter system and a measurement pickup system measuring at least one of amplitude of magnetic Barkhausen noise and coercive field strength and producing measured values;
    (b) electronic evaluation means connected to said measurement pickup system for processing the measured values of the coercive field strength and the amplitude of the magnetic Barkhausen noise in parallel;
    (c) said electronic evaluation means including at least one memory having calibration data or calibration functions for at least one material relating to dependencies between the Barkhausen noise amplitude, the coercive field strength, the hardness and the mechanical stress; and
    (d) said electronic evaluation means including a conversion stage converting the measured values into material properties of hardness and stress using the calibration data stored said at least one memory.

11. Apparatus according to claim 10, wherein said exciter system and said measurement pickup system are movable along a defined measurement path at a defined speed in a region of a component to be tested.

12. Apparatus according to claim 10, wherein said exciter system and said measurement pickup system are movable along defined measurement path at a defined speed in a region of a turbine blade to be tested.

13. Apparatus according to claim 11, wherein said exciter system is a magnetic exciter system also forming a magnetic holder for said measurement pickup system on the component to be tested.

14. Apparatus according to claim 12, wherein said exciter system is a magnetic exciter system also forming a magnetic holder for said measurement pickup system on the component to be tested.

15. Apparatus according to claim 13, wherein said magnetic exciter system includes a magnet yoke having two magnetic poles between which said measurement pickup system is movable.

16. Apparatus according to claim 14, wherein said magnetic exciter system includes a magnet yoke having two magnetic poles between which said measurement pickup system is movable.

* * * * *